US010000304B2

(12) United States Patent
Moncayo, Jr.

(10) Patent No.: US 10,000,304 B2
(45) Date of Patent: Jun. 19, 2018

(54) METHOD FOR SANITIZING AND FILLING CONTAINERS

(71) Applicant: Arthur Moncayo, Jr., Panorama City, CA (US)

(72) Inventor: Arthur Moncayo, Jr., Panorama City, CA (US)

(*) Notice: Subject to any disclaimer, the term of this patent is extended or adjusted under 35 U.S.C. 154(b) by 615 days.

(21) Appl. No.: 14/281,689

(22) Filed: May 19, 2014

(65) Prior Publication Data
US 2015/0329225 A1    Nov. 19, 2015

(51) Int. Cl.
*B65B 3/04* (2006.01)
*G06Q 20/10* (2012.01)
*B65B 55/04* (2006.01)
*B65B 7/28* (2006.01)
*B65B 55/06* (2006.01)
*B65B 55/10* (2006.01)
*B65B 57/00* (2006.01)
*G06Q 20/18* (2012.01)
*G07F 13/02* (2006.01)

(52) U.S. Cl.
CPC ........... *B65B 55/04* (2013.01); *B65B 3/04* (2013.01); *B65B 7/28* (2013.01); *B65B 55/06* (2013.01); *B65B 55/10* (2013.01); *B65B 57/00* (2013.01); *G06Q 20/10* (2013.01); *G06Q 20/18* (2013.01); *G07F 13/02* (2013.01)

(58) Field of Classification Search
CPC .. B65B 3/04; B65B 7/28; B65B 55/00; B65B 55/06; B65B 55/10; B65B 55/12; B65B 57/00; G06Q 20/10; G06Q 20/18; A61L 2/07; A61L 2/16; A61L 2/206
USPC ......... 53/75, 76, 266.1, 426, 493; 422/3, 26, 422/28, 34
See application file for complete search history.

(56) References Cited

U.S. PATENT DOCUMENTS

| | | | |
|---|---|---|---|
| 5,427,682 A | 6/1995 | Vogel et al. | |
| 5,587,089 A | 12/1996 | Vogel et al. | |
| 5,634,501 A * | 6/1997 | Walshe | A61L 2/24 134/113 |
| 5,928,516 A * | 7/1999 | Hopkins | B65D 81/22 210/232 |
| 6,421,986 B1 * | 7/2002 | Dharssi | B65B 61/20 53/415 |
| 6,558,640 B1 * | 5/2003 | Nottingham | A61L 2/06 219/400 |
| 6,752,959 B2 * | 6/2004 | Smith | A61L 2/208 141/89 |
| 7,571,586 B1 | 8/2009 | Morales | |
| 7,895,938 B2 * | 3/2011 | Chang | A61L 2/07 392/303 |
| 8,123,086 B2 * | 2/2012 | Haley | B65D 47/06 215/309 |
| 8,124,011 B2 | 2/2012 | Iwashita et al. | |
| 8,360,272 B2 | 1/2013 | Piersant et al. | |
| 8,865,065 B2 * | 10/2014 | Kain | A61L 2/24 422/1 |
| 8,973,822 B2 | 3/2015 | Brown | |
| 2002/0033943 A1 * | 3/2002 | Clauberg | G01N 21/9081 356/240.1 |
| 2002/0085971 A1 * | 7/2002 | Raniwala | A61L 2/186 422/303 |
| 2003/0095891 A1 * | 5/2003 | O'Neal | A61L 2/07 422/26 |
| 2008/0260907 A1 * | 10/2008 | Mazur | A61L 2/10 426/66 |
| 2009/0205747 A1 * | 8/2009 | Lillard, Jr. | B67D 1/0888 141/94 |
| 2010/0024913 A1 | 2/2010 | Howard et al. | |
| 2011/0110821 A1 | 5/2011 | Iwashita et al. | |
| 2012/0222938 A1 | 9/2012 | Rose et al. | |
| 2012/0318767 A1 | 12/2012 | Burgess et al. | |
| 2013/0011297 A1 * | 1/2013 | Walsh | A61L 2/07 422/26 |
| 2013/0240079 A1 | 9/2013 | Petrini | |
| 2013/0240084 A1 | 9/2013 | Carter et al. | |
| 2014/0284239 A1 * | 9/2014 | Espinosa | B65D 81/00 206/459.5 |

(Continued)

FOREIGN PATENT DOCUMENTS

| | | |
|---|---|---|
| EP | 1958879 | 8/2008 |
| WO | WO-2012/047916 | 4/2012 |

OTHER PUBLICATIONS

Albrecht, Carl, "What is bisphenol A?", Aug. 2010, Health24, Jun. 2011.*
Wikipedia, "Closure (container)", May 30, 2010, https://web.archive.org/web/20100530025821/http://en.wikipedia.org/wiki/Closure_(container).*
NRDC, "Chemicals in Plastic Bottles", May 2008.*
http://www.oberk.com/packaging-crash-course/5-questions-about-autoclaving-plastic-bottles-and-glass-bottles Jonathan, "5 Questions About Autoclaving Plastic Bottles and Glass Bottles", Jan. 15, 2013*
Ayala, A1 Water Store. Purified Water in NJ, published May 22, 2013, https://www.youtube.com/watch?v=xuHkKs7bXs&feature=youtu.be.

(Continued)

*Primary Examiner* — Gloria R Weeks
*Assistant Examiner* — William A Weller
(74) *Attorney, Agent, or Firm* — Morrison & Foerster LLP

(57) ABSTRACT

The present disclosure relates in some aspects to methods and apparatuses for sterilizing, sanitizing, and/or otherwise removing contaminants from, filling, and/or capping containers, such as bottles. In some aspects, the containers are reusable bottles containing or designed to hold drinking water. In some embodiments, the container is received from a customer and/or is provided to the customer. In some embodiments, the methods include returning the same container to the customer. In some embodiments, the methods provide sanitary, convenient, and/or environmentally-friendly alternatives to available methods for removing cleaning, sanitizing, sterilizing, filling, and capping of containers holding drinking liquids.

14 Claims, No Drawings

(56) References Cited

U.S. PATENT DOCUMENTS

2015/0101286 A1* 4/2015 Clarkson ............... B08B 9/0826
53/426

OTHER PUBLICATIONS

Product description for the BWF60 Washer/Filler/Capper by Norland International, Inc., retrieved from the Internet Jun. 3, 2015, 2 pages.
Product description for Triton450™ from Norland International, retrieved from the Internet Jun. 3, 2015, 1 page.

* cited by examiner

METHOD FOR SANITIZING AND FILLING CONTAINERS

FIELD

The present disclosure relates in some aspects to methods and apparatuses for sterilizing, cleaning, disinfecting, sanitizing, filling (e.g., refilling), and/or capping containers, such as bottles. In some aspects, the containers are reusable bottles containing or designed to hold drinking water. In some embodiments, the container is received from a customer and/or is provided to the customer, e.g., sold to the customer. In some embodiments, the methods include returning the same container to the customer following the method steps, such as the sterilizing, filling, and/or capping. In some embodiments, the methods provide sanitary, convenient, and/or environmentally-friendly alternatives to available methods for removing cleaning, sanitizing, sterilizing, filling, and capping of containers holding drinking liquids.

BACKGROUND

Various methods for cleaning, disinfecting, sanitizing, sterilizing, filling, and/or capping of containers, including bottles are available. Available methods have not been entirely satisfactory. Improved methods are needed. For example, methods, apparatuses, models, facilities, and systems are needed for sanitizing or sterilizing, filling, and/or capping containers, and receiving and providing the same from customers. For example, such methods, apparatuses, and systems are needed that are cost-effective, more accessible, convenient, sanitary, hygienic, and/or environmentally friendly. Provided herein are methods, apparatuses, models, systems, and facilities addressing these needs.

SUMMARY

Provided are methods, apparatuses, business models, systems, and facilities, for the treatment and filling of containers and the provision and receipt of the containers from customers. In some aspects, the embodiments provide cost-effective, convenient, sanitary, hygienic, and/or environmentally-friendly advantages compared to available methods and apparatuses. For example, in some aspects, the methods and apparatuses offer access to clean, sanitary, hygienic drinking water filling and storage to customers who may otherwise not have such access. Such customers include individuals, such as those living in low-income, densely populated, remote, or developing areas or regions, college students or others living on college or school campuses or other dormitories, and those who do not have access to or cannot afford drinking water delivery services and, customers who would otherwise use water refill kiosks. Also among the customers are businesses and other entities, such as non-profit organizations and universities, and their agents.

In some embodiments, the provided methods are carried out by receiving a container from a customer, removing contaminants from the container, and providing the container from which contaminants have been removed to the customer.

In some embodiments, the provided methods are carried out by removing contaminants from a container and providing the container from which the contaminants have been removed to a customer, where the providing does not include delivery to a home or business owned or rented by the customer.

In some aspects, the methods further include filling the containers from which contaminants have been removed with a substance, typically before providing the container to the customer, or providing a substance dispensing station to the customer, with which to fill the container. The substance generally is a consumable substance, e.g., consumable liquid, such as drinking water.

In some aspects, the methods further include capping or otherwise closing or sealing the container after filling or refilling it with the substance. In some aspects, the capping includes attaching a cap, such as an airtight, sealed cap to the container, such as to an opening or outlet of the container, such as one designed for insertion into a dispenser such as a drinking water dispenser, or to which a spout will be attached for later use. In some aspects, the attachment forms an airtight seal between the cap and the bottle.

In some embodiments, the sterilizing or sanitizing is carried out by inserting the container, e.g., bottle, into a machine configured and/or programmed to sterilize or sanitize and/or wash the container. In some aspects, the machine is further configured to fill the container with the substance and the filling is carried out using the same machine or a different machine configured and/or programmed to fill the container with the substance, such as the drinking water.

In some aspects, the various method steps, such as the providing and/or the receipt of the containers, the removal of contaminants (such as sterilizing or sanitizing), the filling, refilling, and/or capping of the containers, is carried out in a store or other location, such as one that is owned, leased, or operated by a service provider, generally the service provider carrying out the methods or whose agent is carrying out the methods.

In some aspects, the method further includes inspecting a container owned by the customer, prior to the removal of contaminants, to determine one or more properties of the materials from which the container is made, such as the presence, absence, or an amount of BPA contained in the container, or the recycling code assigned to the container. In some aspects, the methods further include informing the customer of such information and recommending use of a different container. For example, in some aspects, where the inspecting reveals BPA in the container owned by or brought by the customer, the methods further include offering for sale to the customer a container substantially free of BPA, and/or one containing less than 1, 0.5, 0.1, 0.05, or 0.01 weight percent of BPA-based polycarbonate or other material. In some aspects, this container (e.g., the one substantially free of BPA) is the container used in subsequent method steps, such as removal of contaminants, filling, capping, and provision to the customer.

In some embodiments, the methods further include delivery to a home or business of the customer, or accompanying the customer to such a location with the container.

In some embodiments, the customer owns or has rented the container, such as from the service provider carrying out the methods or from a third party. In some embodiments, the container contains an identifier, such as for association of the bottle with the customer. In some aspects, the methods further include applying such an identifier to the container being treated and/or refilled, for association of the container with the customer. In some aspects, the methods include inspecting the identifier prior to returning or providing the container to the customer to ensure that the customer is provided his or her bottle.

In some embodiments, the methods further include accepting payment from the customer. In some aspects, the payment is not made on a subscription or recurring basis or the customer does not have a subscription or recurring payment set up with the service provider carrying out the methods. In some aspects, the methods are carried out on a pay-per-use or pay-per-service basis.

Also provided are apparatuses for carrying out the removal of contaminants, filling, and/or capping of containers, such as bottles, and for the interaction with customers wishing to receive such services. In some embodiments, provided are apparatuses for sterilizing or sanitizing, filling, and vending containers, such as bottles. In some aspects, the apparatus includes a decontamination station, such as a sterilization or sanitization station, configured to receive and remove contaminants from, e.g., sterilize or sanitize, the container. In some aspects, the apparatus further includes a container filling station configured to receive the container following sterilization or sanitizing, for filling with a liquid. In some aspects, the apparatus further includes a liquid source configured to supply the liquid to the container, for example, when it is present in the filling station. In some aspects, the apparatus further includes a capping station or other device for applying a cap or other seal to the container, such as after filling. In some aspects, the apparatus further includes a payment acceptor, configured to accept payment from a customer, for example, in exchange for the decontamination, filling, and/or capping services, and or the provision of the containers. In some aspects, the apparatus further includes one or more controllers, such as a controller operatively connected to the contaminant removal station, liquid source, and/or payment acceptor. In some embodiments, the controller is operative to cause the decontamination, e.g., sterilization or sanitization, and filling of the container upon receipt of payment by the payment acceptor. In some aspects, the apparatus further includes a screen for interaction between the controller and the customer, one or more vending shelves, doors, and/or conveyor belts, for receipt and dispensing of the containers, such as bottles. The apparatus generally includes one or more sensors, for sensing whether the containers are in a particular location or have been treated in a particular way, such as whether they have been sterilized, filled, and/or capped.

Among the containers are bottles, vessels, jugs, cans, barrels, kegs, growlers, jars, cups, boxes, buckets, beakers, flasks, bags, pouches, and other vessels. In some embodiments, the containers are designed to store liquids, for example, for later consumption, such as drinking water. In some aspects, the containers, e.g., bottles have a liquid holding capacity of at least at or about, or at or about, or greater than at or about 2, 2.5, 3, 3.5, 4, 4.25, 4.5, 4.75, or 5 gallons, at or about, at least at or about, or greater than at or about, or less than at or about 0.05, 0.1, 0.2, 0.25, 0.5, 1, 2, 3, 4, or 5 liters. In some embodiments, the container can fit into a standard liquid dispenser. In some embodiments, the bottle is substantially free of BPA and/or contains less than at or about 1, 0.5, 0.1, 0.05, or 0.01 weight percent of BPA-based polycarbonate or other BPA-containing material.

The removal of contaminants generally includes sterilizing or sanitizing the container, and can in some aspects include cleaning or washing the containers. In some embodiments, the sterilizing or sanitizing is carried out by exposing the container to steam and/or water at a temperature of at least about 130, 140, 150, 160, 170, 180, 190, or 200° F. or more. In some aspects, the sterilizing or sanitizing is carried out by applying boiling water to the container. In some embodiments, it is carried out by exposing the bottle to a reactive gas such as ozone. In some embodiments, it is carried out without using ozone or without using a substance that is harmful to human health, toxic, or contains known carcinogens.

DETAILED DESCRIPTION

All publications, including patent documents, scientific articles and databases, referred to in this application are incorporated by reference in their entirety for all purposes, to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference. The section headings used herein are for organizational purposes only and are not to be construed as limiting the subject matter described.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

1. Provided Methods and Systems

Provided are methods, apparatuses, systems, and facilities for the handling and treating of containers, such as bottles, and for the receipt and provision of the containers from and to customers. In some embodiments, the methods include cleaning, e.g., washing, sanitizing, and/or sterilizing the containers. In some embodiments, the methods include filling the containers, typically with water, such as purified water or drinking water. In some embodiments, the methods include capping the containers, such as with a sealable cap. In some embodiments, the methods include providing the container to a customer and/or receiving the container from a customer. For example, in some aspects, the container is purchased, rented, or loaned to the customer. In some aspects, it is received from the customer, cleaned, refilled, and/or capped, and returned to the customer. In some embodiments, the customer owns the bottle. In some embodiments, the service provider carrying out the methods owns the bottle.

In some aspects, one or more, e.g., all, of the steps are carried out in a store, such as a store owned or leased by a service provider. In some embodiments, they are carried out at or in a kiosk, such as one owned, leased and/or controlled by the service provider. In some embodiments, the service provider physically carries out or causes to be carried out the cleaning, sanitizing, disinfecting, sterilizing, filling, refilling, and/or capping of the containers. In some aspects, one or more steps are carried out in a machine, such as a sterilizing or sanitizing, filling, and/or capping machine. When it is said that the service provider physically carries out the methods, this can include an agent of the service provider carrying out the methods where the service provider is a business or other non-individual entity. In some aspects, the customer and/or the service provider operates one or more of the machine(s). In some aspects, the customer operates the machine(s) with the oversight and/or direction of the store owner or service provider. When it is said that the customer carries out the steps, again, this can include an agent of the customer carrying out the steps where the customer is a business or other non-individual entity. In some embodiments, the method and/or steps of the method are carried out while the customer waits in the store or at the kiosk. In some embodiments, the bottle is delivered at the end of the methods to the customer, for example, in his or her home or office.

In some aspects, the provided methods, systems, and apparatuses provide various advantages compared to available methods and apparatuses for filling and/or sterilizing or sanitizing containers, such as bottles for drinking water. For example, available methods and apparatuses include delivery and subscription-based services, through which customers receive filled and capped bottles of drinking water and return used bottles. Available methods and apparatuses also include vending machines and kiosks through which customers can refill reusable water bottles or jugs. Such methods and systems can have drawbacks, such as not being convenient, accessible to all or certain customers, geographical areas, or demographics, not being environmentally friendly or being less environmentally friendly than desired, and/or posing health or sanitation risks. In some aspects, the customers are those living and/or working in a densely populated, urban, or metropolitan area, such as a city or downtown area. For example, individual users of reusable water bottle refilling machines can be concerned regarding maintenance of proper hygiene, health, and/or sanitation associated with the reusable bottles. Provided are methods and apparatuses that address these concerns and drawbacks.

In some embodiments, the provided methods and apparatuses provide sterilizing or sanitizing, filling, and capping services to customers in a relatively more convenient or accessible manner, such as those which are more convenient, accessible, and/or affordable to a broader range of customers or customer bases, or to certain demographics or neighborhoods, including lower-income customers or customers living in relatively less-developed areas. In some embodiments, the provided embodiments have the advantage of providing improved sanitation, health, or hygiene, and or being environmentally-friendly or eco-friendly. For example, in some aspects, the containers are selected based on their materials or manufacturing process carrying a reduced likelihood of harm to individuals, such as the customer or user, and/or to the environment. In some aspects, the containers are free, substantially free, or contain relatively low levels of harmful substances, such as Bisphenol A (BPA), or does not leach a harmful substance into a liquid housed therein. Exemplary materials are polyethylene terephthalate, High Density Polyethylene (HDPE), Low Density Polyethylene (LDPE), and Polypropylene. In some aspects, they are recyclable and/or are made using a process that emits or produces relatively fewer harmful chemicals, gasses, or others substances compared to others.

In some embodiments, the methods further include counseling, informing, or advising the customer regarding features of the containers, caps, sterilization or sanitization process, and/or water in terms of their safety, impact on or relative safety or risk with respect to health, safety, and/or environmental factors.

2. Containers and Other Materials

Among the containers are vessels, bottles, jugs, cans, barrels, kegs, growlers, jars, cups, boxes, buckets, beakers, flasks, bags, pouches, and other vessels. In some embodiments, the containers are designed to store liquids, for example, for later consumption. In some aspects, the containers are sealed, capped, or otherwise closed, for example, to promote safety or convenience associated with storage of liquids. Exemplary sealing or closing features include caps, lids, spouts, corks, and seals, such as industrial caps or seals. In some aspects, the seal, cap, or lid provides air-tight storage of the liquid or other matter contained within the container. In some aspects, the containers are food-grade containers. In some aspects, the containers have handles or other carrying devices.

Among the containers and/or other materials used with the containers, such as caps, lids, spouts, and seals, are manufactured with one or more materials, such as glass, metal, rubber, and typically plastic, such as thermoplastics and bioplastics, including those made from polyalkylene carbonates such as polyethylenes or polypropylenes. Particular examples are polyethylene terephthalate, High Density Polyethylene (HDPE), Low Density Polyethylene (LDPE), and Polypropylene. In some embodiments, the containers are plastic containers, such as bottles and/or jugs. Exemplary materials are terephthalate based polyester comprising 2,2,4,4-tetramethyl-1,3-cyclobutanediol residues and 1,4-cyclohexamedimethanol residues.

In some embodiments, the containers are made with materials that are environmentally-friendly and/or reduce or eliminate one or more harms to the user, such as by reducing the likelihood of leaching of harmful chemicals, e.g., hormones or carcinogens, into consumable materials, such as drinking water or other liquids that could then be ingested by a user. In some aspects, the containers are free of or have relatively low levels of Bisphenol A (BPA), a chemical commonly used in production of polycarbonate and epoxy resins and/or plastics and other materials, such as in plastic bottles, and which can be harmful to human health. In some embodiments, the bottle is substantially free of BPA. For example, in some aspects, the bottle or container contains less than 1, 0.5, 0.1, 0.05, or 0.01 weight percent of BPA-based polycarbonate.

In some embodiments, the container is not made of or does not contain polyvinyl chloride (PVC), does not contain di-2-ethylhexyl phthalate (DEHP), does not contain polystyrene (PS) or styrene, does not contain polycarbonate. In some embodiments, the container does not leach a harmful substance, such as a hormone disrupter or endocrine disrupter or human carcinogen into liquid, such as water, housed in the container, for example, when the container heated to a temperature of at least at or about 100° F., 120° F., 130° F., 140° F., or 150° F., or higher. In some aspects, the container is recyclable. In some aspects, the container has a recycle code #1, #2, #4, or #5, and/or does not have a recycle code 3, 6, and/or 7. In some aspects, the materials are selected based on the relatively low impact of their production on the environment, such as the relatively low emission of harmful gasses or other chemicals that occurs during production.

In particular embodiments, such a container is provided to, e.g., sold, to a customer. In some embodiments, the customer exchanges a container, e.g., bottle or jug, having less desirable features, for one that is more desirable in terms of environmental or health risks. In some embodiments, from which type of material the container is made influences one or more steps of the methods, such as whether the container is sterilized, e.g., using a certain degree or type of heating process, or whether it is simply washed or sanitized.

In some embodiments, the container is designed to store liquid or other consumable until opening, whereupon the liquid or other consumable will be consumed without recapping and further storage. In other embodiments, the container and process is designed to allow repeated access and continued storage of the liquid or other matter in the container, such as a drinking water jug or bottle for daily use. Thus, in some examples, the containers are designed for use with or include spouts or dispensers, such as dispensers or spouts for drinking water. In some embodiments, they are designed to store the liquid or other matter at room temperature; in some embodiments, they are designed for storage at frozen or refrigerated temperatures, such as at or below at or about 40° F. or 4° C., or at or below at or about 0° F. or −18° C.

In some embodiments, the container has a liquid holding capacity of at least at or about, or at or about, or greater than at or about 2, 2.5, 3, 3.5, 4, 4.25, 4.5, 4.75, or 5 gallons. In some embodiments, the container has a liquid capacity of at or about, at least at or about, or greater than at or about, or less than at or about 0.05, 0.1, 0.2, 0.25, 0.5, 1, 2, 3, 4, or 5 liters. In some embodiments, the container has a weight of at least at or about 600, 650, 700, or 725 grams and/or not more than at or about 900, 850, 800, or 775 grams. In some embodiments, the container can fit into a standard liquid dispenser. In some embodiments the container has a maximum diameter of at or about 6, 8, or 10 inches and/or not more than at or about 18, 14, or 12 inches.

In some embodiments, the container is a bottle designed to fit into a standard liquid, e.g., drinking water, dispenser. In some aspects, the bottle has an outlet, such as for dispensing of the liquid. In some embodiments, the outlet is present at a first end of the bottle and the bottle further includes a base at a second end of the bottle, and a main body located between the outlet and base. In some embodiments, the capping includes placing a cap over the outlet. In some embodiments, the bottle or other container includes a handle.

Exemplary containers and bottles are those disclosed in U.S. Patent Application, Publication No.: US20120318767 A1, Burgess et al., Dec. 20, 2012, and in European Patent No. EP EP1958879B1, Iwashita et al., Jul. 11, 2012, U.S. Patent Application Publication No.: US2011110821 (A1), Iwashita, May 12, 2011, and U.S. Pat. No. 8,124,011, Feb. 28, 2012, (B1).

3. Customers and Receipt and Provision of the Containers

The methods generally include providing sterilized containers, such as bottles, to customers. In some aspects, they further include receipt of the containers from customers, and/or other interactions with the customers, including provision of access to customers of machines and apparatuses, such as kiosks as described herein.

In some embodiments, the customer is an individual. In some aspects, the individual customer is a low income customer or a customer living in an area in which drinking water delivery service is not available or not affordable. Among the individual customers are those living and/or working in urban, metropolitan, non-suburban, or densely populated areas, such as a major metropolis, those living low-income areas, non-developed or relatively less developed areas, and those living in apartment or condominium complexes, dormitories, or other multi-family dwellings, including college students and others living on college or school campuses, customers who otherwise would use or have previously used water refill kiosks, and customers living in developing countries or areas. In some embodiments, the customer is a business or non-individual entity, including non-profit organizations, universities, and other educational or research entities, or agent thereof, such as one located in an urban, metropolitan, non-suburban, or densely populated area, such as a major metropolis, a low-income, non-developed, developing, or relatively less developed country or area, and those within multi-unit buildings or structures. In general, when the customer is a business or other entity, the receipt from the customer and/or the provision to the customer is from and/or to an agent of the customer, which is an individual.

In some embodiments, the methods include receiving a container, e.g., a bottle, from a customer or agent of the customer. In some embodiments, the methods include providing, e.g., selling or renting, a container to the customer, for example, a container having been sterilized by the methods. In some embodiments, the container received from the customer is used in the sterilization, filling, capping and/or other steps. In other embodiments, the container received from the customer is determined not to be suitable or ideal for use, for example, by inspecting the container and/or by inquiring from the customer regarding the materials from which the container is made. For example, in some aspects, it is learned by inspection or inquiry that the container includes one or more harmful substances, which may be harmful to the environment and/or the user of the container, such as BPA and/or other harmful substance. In some such embodiments, a more suitable container is provided, e.g., sold, to the customer and sterilized, cleaned, sanitized, filled, and/or capped.

In some embodiments, the receipt of the container from the customer and/or the provision of the container to the customer does not occur at a home or place of business of the customer or owned or rented by the customer. Thus, in some embodiments, the method provides the advantage of being accessible to customers working or living in geographic areas in which home or office pickup and/or delivery of containers of drinking water or other liquid is not provided or available or is not feasible. In some aspects, the receipt of the container from the customer occurs in a store or other location owned, operated, or leased by the service provider carrying out the methods, such as a market, grocery store, community center, or storage facility. In some embodiments, the location is a brick-and-mortar location, such as one located in a densely populated, urban, or metropolitan area, such as a city or downtown area. In some embodiments, the provision and/or receipt of the containers is carried out through an apparatus, such as a kiosk, designed for receipt, sterilizing, refilling and/or capping, and dispensing the bottles. In other embodiments, the receipt of the container from the customer and/or the provision of the container to the customer occurs at a home or place of business of the customer or owned or rented by the customer.

In some embodiments, the container includes (e.g., is tagged with) an identifier associated with the customer. In some aspects, the identifier is unique to the customer, such that only a bottle or bottles owned or leased by the particular customer include the identifier, permitting identification of the container as associated with the customer. In some embodiments, the methods further include tagging the container with or otherwise applying the identifier to the container. Applying the identifier typically is done upon or soon after receipt from or sale or rental to the customer, such as prior to sterilization, filling, and recapping, and/or prior to insertion of the container into a machine configured to carry out such steps. Exemplary identification codes are bar codes and combinations of numbers and/or letters.

In some embodiments, the methods further include inspection of the container prior to provision to the customer, e.g., to determine the identity of the customer by inspecting the identifier. In some aspects, the inspection is carried out by the machine or apparatus used to fill, sterilize, sanitize, and/or cap the container, and/or another machine or apparatus, such as one including a bar code or electronic code reader.

In some embodiments, the methods further include delivery of the container to the customer and/or accompanying the customer to his or her home or office to provide the bottle or other container.

In some embodiments, the methods further include accepting payment from the customer for the services and products provided. In some aspects, the customer is a pay-per-service, pay-per-product, or pay-per-use customer. In some aspects, the customer is not enrolled in a recurring payment plan or subscription service, is not obligated to make future payments, and/or has not pre-paid in advance. In some aspects, the customer is not renting or has not rented a cooler from the service provider carrying out the methods. In some aspects, the customer is an individual. In some aspects, the customer lives in a region in which a large water bottle delivery service is not available.

In some aspects, the methods are carried out while the customer waits in the store or other location owned, rented, or operated by the service provider carrying out the methods. In some aspects, the method steps, e.g., the sterilizing, filling, and/or capping are carried out in less than at or about 10, 9, 8, 7, 6, 5, 4, 3, or 2 hours, such as less than at or about 60, 50, 40, 30, 20, 15, 10, or 5 minutes.

4. Sterilizing and Other Steps for Removing Contaminants

In some embodiments, the methods include treating the bottle or other container to remove, ensure the continued absence or relatively low level of, or minimize one or more contaminants, generally prior to filling or refilling of the container, for example, sterilization. In some aspects, such treatment includes cleaning, disinfecting, and/or typically sanitizing or sterilizing, typically sterilizing. As used herein, the terms "sanitize" and "sterilize" refer to decontamination processes that eliminate, reduce, or prevent or reduce accumulation of harmful microorganisms from the thing being sterilized or sanitized, such as the container or cap, for example, levels acceptable for human use. "Sterilizing" refers to a process capable of eliminating, preventing the accumulation of, or killing all forms of microorganisms, including transmissible agents such as fungi, bacteria, viruses, and spore forms, present in or on the thing being sterilized. "Sanitizing," on the other hand, can encompass a process that eliminates, prevents accumulation of, or kills only a selective number of agents, such as only bacteria or viruses or only certain types of bacteria. In some embodiments, the sanitation is sterilization. A specific sterilization or sanitation method can be specified.

In some embodiments, any of a number of cleaning, sanitizing, disinfecting, and/or sterilizing methods may be used. In some examples, the methods for sterilization are selected to minimize harmful effects on the user, consumer, operator of the methods, and/or the environment. In some examples, the container is sterilized or sanitized without the use of ozone.

In some embodiments, the sterilization or sanitization is carried out using heat, such as by steam or hot liquid. In some embodiments, the sterilization is carried out by chemical sterilization or radiation. Among the chemicals for sterilization or sanitization are ethylene oxide, nitrogen oxide, ozone, bleach, glutaraldehyde, formaldehyde, phthalaldehyde, hydrogen peroxide, peracetic acid, or silver. Available sterilization or sanitization methods include steam, heat, irradiation, pressure, injecting water, gas, or a chemical sterilizer or sanitizer into the bottle, autoclaving, or a combination thereof. In some embodiments, the water, gas, or sterilizer or sanitizer is heated and/or has a sterilizing effect. In some embodiments, the sterilization is carried out using steam, i.e., steam sterilization, for example, using an autoclave, and/or other method of applying heat, such as washing with heated water. In some embodiment, the steam is heated to between at or about 121° C. and at or about 134° C. (250-273° F.).

In some aspects, the heat-based sterilization or sanitization, e.g., exposure to heated water, steam, or other heat source, is carried out for at least at or about 1, 2, 3, 4, 5, 10, 15, 18, 20, 25, 30, or 60 minutes. In some aspects, it is carried out for between 3 and 60 seconds, e.g., between 3 and 20 seconds, such as by injection of heated water and/or induction of slightly positive pressure in the inside of the container. In some examples, the steam sterilization is carried out at least at or about 121° C. (250° F.), or at least at or about 200, 175, 170, 165, 160, 155, 150, 145, or 140° F., or at least about 60, 65, 70, 75, 80, 85, 90, or 95° C., such as between at or about 65° C. and at or about 90° C.

In some embodiments, the sterilization or sanitization is carried out at a certain pressure, such as a slightly positive pressure, or a pressure of at least at or about 1, 2, 3, 4, 5, 6, 7, 8, 9, 10, 15, or 20 kPa, such as between at or about 1 and at or about 20 kPa, or of at least at or about 100 kPa (15 psi). In some aspects, the sterilization or sanitization is carried out by injecting heated water or other heated fluid into the container, such as the bottle, or at least onto the inner surface of the container. In some aspects, the container is put into an inflated state by producing a slightly positive pressure, e.g., between at or about 1 and at or about 20 kPa in the bottle by causing the hot water or other hot liquid to be stored in a mouth or outlet portion of the container in an inverted state or injecting air into the container.

In some aspects, combinations of any such temperatures, durations, and/or pressures, are used. In some aspects, indicator tape, meters, charts, and/or other indicators of proper temperature, pressure, and/or period of time, are used to ensure the desired degree of sterilization. In some examples, a chemical in the tape will change color when the appropriate conditions have been met. In some aspects, the methods include inquiring of the customer and/or inspecting the container to determine whether the container is manufactured using any materials or chemicals that could be harmful to the user or the environment, such as BPA, hormones, and/or carcinogens, such as examples discussed herein. In some aspects, if it is determined that the container includes such harmful substance(s), the sterilization is carried out by a method other than a heat-based method or other than steam, and/or the bottle is merely cleaned or disinfected or sanitized as opposed to sterilized.

In some embodiments, the sterilization or sanitization is carried out by applying one or more chemicals. Chemical sterilization may be appropriate, for example, where the material of the container is not amenable to heat or steam-based sterilization methods, for example, where the container is manufactured using a BPA-containing material or material containing another harmful chemical, such as a carcinogen, which could leach into the liquid in the container if heat or steam were used.

In some examples, the chemical sterilization or sanitization is carried out using low temperature gas sterilizers, which function by exposing the container to high concentrations (such as 5-10% v/v) of very reactive gases (such as alkylating agents such as ethylene oxide, and oxidizing agents such as hydrogen peroxide and ozone).

In some embodiments, the sterilization or sanitization is carried out using ozone. In other embodiments, the sterilization is carried out without using ozone or without using other chemicals. Ozone is a sterilizing gas commonly used in industrial settings to sterilize water, air, and/or to disinfect surfaces. Ozone can oxidize most organic matter. In some respects, ozone offers advantages as a steriliant gas. For example, it possesses strong oxidizing properties (E=2.076 vs SHE, CRC Handbook of Chemistry and Physics, 76th Ed, 1995-1996) capable of destroying a wide range of pathogens, including prions without the need for handling hazardous chemicals since the ozone is generated within the sterilizer from medical grade oxygen. The high reactivity of ozone means that waste ozone can be destroyed by passing over a simple catalyst that reverts it back to oxygen and also means that the cycle time is relatively short. On the other hand, it is a toxic and unstable gas that generally is produced on-site, making it impractical in many settings. The gas can be very reactive and hazardous; the NIOSH immediately dangerous to life and health limit for ozone is 5 ppm, 160 times smaller than the 800 ppm IDLH for ethylene oxide. Thus, equipment and processes using ozone generally are continuously monitored for leaks and to provide warning in the event of a leak.

In some aspects, liquid steriliants or sanitizers and high disinfectants are used, such as those including oxidizing agents such as hydrogen peroxide and peracetic acid and/or aldehydes such as glutaraldehyde and/or o-phthalaldehyde.

In some embodiments, the sterilization or sanitization is carried out using hydrogen peroxide. Hydrogen peroxide in some aspects is relatively non-toxic when diluted to low concentrations, such as the familiar 3% retail solutions although hydrogen peroxide is a dangerous oxidizer at high concentrations (>10% w/w). Hydrogen peroxide is strong oxidant and these oxidizing properties allow it to destroy a wide range of pathogens and it is used to sterilize heat or temperature sensitive articles. In medical sterilization hydrogen peroxide is used at higher concentrations, ranging from around 35% up to 90%. The biggest advantage of hydrogen peroxide as a sterilant is the short cycle time. Whereas the cycle time for ethylene oxide may be 10 to 15 hours, the use of very high concentrations of hydrogen peroxide allows much shorter cycle times. Some hydrogen peroxide modern sterilizers, such as the Sterrad NX have a cycle time as short as 28 minutes.

Hydrogen peroxide sterilizers in some aspects can have certain drawbacks. Since hydrogen peroxide is a strong oxidant, there can be material compatibility issues and users should consult the manufacturer of the article to be sterilized to ensure that it is compatible with this method of sterilization. The penetrating ability of hydrogen peroxide may not be as good as ethylene oxide and so there can be limitations on the length and diameter of lumens that can be effectively sterilized.

While hydrogen peroxide in some aspects offers significant advantages in terms of throughput, as with all sterilant gases, sterility is achieved through the use of high concentrations of reactive gases. Hydrogen peroxide is primary irritant and the contact of the liquid solution with skin will cause bleaching or ulceration depending on the concentration and contact time. The vapor is also hazardous with the target organs being the eyes and respiratory system. Even short term exposures can in some contexts be hazardous; NIOSH has set the Immediately Dangerous to Life and Health Level (IDLH) at 75 ppm. less than one tenth the IDLH for ethylene oxide (800 ppm). Prolonged exposure to even low ppm concentrations can cause permanent lung damage and consequently OSHA has set the permissible exposure limit to 1.0 ppm, calculated as an 8 hour time weighted average (29 CFR 1910.1000 Table Z-1). Even though the sterilizer manufacturers go to great lengths to make their products safe through careful design and incorporation of many safety features, workplace exposures of hydrogen peroxide from gas sterilizers are documented in the FDA MAUDE database. When using any type of gas sterilizer, prudent work practices will include good ventilation (10 air exchanges per hour), a continuous gas monitor for hydrogen peroxide as well as good work practices and training.

Vaporized hydrogen peroxide (VHP) is used to sterilize large enclosed and sealed areas such as entire rooms and aircraft interiors.

Dry sterilization process (DSP) uses hydrogen peroxide at a concentration of 30-35% under low pressure conditions. This process achieves bacterial reduction of 10-6 . . . 10-8. The complete process cycle time is just 6 seconds, and the surface temperature is increased only by 10-15° C. (18 to 27° F.). Originally designed for the sterilization of plastic bottles in the beverage industry, because of the high germ reduction and the slight temperature increase the dry sterilization process is also useful for medical and pharmaceutical applications.

In some embodiments, such chemical sterilization methods are not used. In some embodiments, the use of gas and liquid chemical sterilants/high level disinfectants can avoid the risk of heat damage or leaching of harmful chemicals from the container material. On the other hand, such chemicals can carry the risk of harm to the operator of the methods and/or to the consumer or user of the container or drinking water. Thus, in some embodiments, the sterilization is carried out by a method other than chemical sterilization.

In some embodiments, the removal of contaminants is carried out by, or further includes, cleaning, such as using one or more detergents, or disinfecting using bleach or other sanitizing solution.

In some embodiments, the sterilizing or other contaminant removal step is performed by the service provider. In some aspects, the service provider, e.g., the operator of the methods, carries out the sterilization using a machine, such as an industrial sterilizing machine. Exemplary machines for sterilization include large bottle washers, fillers, and capper machines of the TritonLine™, available from Norland International, such as the Triton450™ (see World Wide Web at www.triton450.com), and/or the BWF60 Washer/Filler/Capper, available from Norland International (see World Wide Web at www.norlandintl.com/BWF60-washer-filler-capperlarge-bottle-water-equipment). In some embodiments, in addition to sterilizing, the machine washes, fills and/or caps the containers. In some embodiments, the customer operates one or more of these aspects of the machine. In some aspects, the machine is operated by the service provider or an agent of the service provider.

In some embodiments, the sterilization or sanitation methods also include those described in European Patent No. EP EP1958879B1, Iwashita et al., Jul. 11, 2012, U.S. Patent Application Publication No.: US2011110821 (A1), Iwashita, May 12, 2011, and U.S. Pat. No. 8,124,011, Feb. 28, 2012, (B1).

5. Filling the Containers and Liquids

In some embodiments, the methods and apparatuses include steps or features providing for filling of the containers, e.g., bottles, with a substance. Typically, the substance is a consumable substance, more typically a consumable liquid, such as drinking water. For example, in some aspects, the sterilized or sanitized bottle is filled with the liquid prior to capping and/or returning or providing the bottle to the customer.

In some examples, the methods provide the advantage of generating or maintaining a sterile or sanitary environment of the container to maintain the liquid or other consumable substance in a state appropriate for human consumption, for a certain period of time and/or under certain conditions. In some embodiments, the containers are filled with drinkable or consumable liquids, such as water, e.g., drinking water, purified water, tap water, spring water, well water, rainwater, recycled water, treated water, distilled water, non-alcoholic beverage such as juice, soda, tea, sports drink, drink with one or more nutritional supplement, meal replacement, formula, milk, and/or alcoholic beverage, such as beer, wine, or other liquor, or medicine or baby product.

In some embodiments, the liquid is water, typically drinking water. In some aspects, the water is tap water; in some aspects, the water is purified water. In some embodiments, the bottle is filled by inserting into or exposing the container to a machine with a filling station and/or liquid source configured to supply the liquid to the bottle. In some aspects, the same machine that is used to sterilize or sanitize and/or cap the bottle also is used to fill the bottle. In some aspects, the filling In some embodiments, the bottle is filled with drinking water prior to being returned to the customer. In some embodiments, the filling step is performed by the service provider, the customer, or an agent of the customer. In some embodiments, the filling step is performed by operating a machine that purifies and/or sterilizes water.

In some aspects, the methods and apparatuses further include or provide for purifying or sterilizing or decontaminating the water, such as by reverse osmosis, exposure to UV, filtration, or other water purification method. For example, in some aspects, the water is purified using a seven-stage reverse osmosis system. In some embodiments, the liquid, e.g., drinking water, is purified and/or sterilized from tap water. In some embodiments, the water purification or sterilization is carried out using heat, irradiation, pressure, filtration, sedimentation, distillation, flocculation, a biological process, a chemical process, ion exchange, disinfection, chlorine disinfection, chlorine dioxide disinfection, chloramine disinfection, ozone disinfection, UV disinfection, or a combination thereof.

In some embodiments, the methods and apparatuses include or include features for testing the water or other liquid for one or more of various properties, including dissolved oxygen content, turbidity, temperature, pH, total dissolved solids (TDS), salinity, water hardness or softness, and the presence of microorganisms, such as water-borne microorganisms. In some aspects, the level of microorganisms, e.g., $E.\ coli$, residual chlorine, pH, and/or turbidity are measured. In some aspects, the presence of ions such as calcium or magnesium, are measured. Other parameters for measuring are fluoride content, lead content, chromium content, and perchlorate content. See Guidelines for Drinking-water Quality, 3rd. ed., Incorporating the First and Second Addenda, Vol. 1, Recommendations, ISBN: 978 92 4 154761 1, available on the World Wide Web at who.int/water_sanitation_health/dwq/fulltext.pdf In some embodiments, the water has a certain oxygen content, such as at or about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, or 8.9, or between at or about 7 and 7.9, 8 and 8.5, or less than at or about 9 or greater than at or about 6 or 6.5 or 6.9, mg/L. In some embodiments, the water has a certain pH, or a pH within a range, such as at or about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, or 8.9, or between at or about 7 and 7.9, 8 and 8.5, or less than at or about 9 or greater than at or about 6 or 6.5 or 6.9. In some embodiments, the TDS is at or about or less than at or about 0, 10, 20, 30, 40, 50, 60, 70, 80, 90, 100, 200, 300, 400, 500, 400-500, 600, 700, 800, 900, or 1000, parts per million (ppm). In some embodiments, the percentage of calcium and/or magnesium ions is between at or about 1-20 or 0-20, such as at or about or below or at least 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20% calcium, magnesium, or both.

In some embodiments, the water is treated or otherwise processed to change, e.g., reduce or increase, one or more of the properties, such as to change the oxygen content, pH, temperature, TDS, salinity, turbidity, hardness or softness, and/or to remove microorganisms. In some examples, the treatment is by the addition of sodium sulfite ($NA_2SO_3$), or other oxygen-reacting chemicals. In some embodiments, chloramine or similar chemical is added.

In some embodiments, the water is tested to determine the one or more features. In some aspects, the methods include communicating the result or results of such testing to the customer, such as by informing the customer of the oxygen content, pH, turbidity, level or presence or absence of microorganisms, e.g., $E.\ coli$, and/or content of residual chlorine in the water. In some aspects, the steps and equipment for carrying out the sterilization, cleaning, disinfecting, sanitizing, washing, capping, and/or filling, are selected at least in part based on the results of such testing.

6. Capping

In some embodiments, the methods and apparatuses further include or provide for capping or otherwise closing of the containers, such as the bottles. Such features can be advantageous, for example, in promoting safety or convenience associated with storage of liquids, particularly liquids for human consumption. Exemplary sealing or closing features include caps, lids, spouts, corks, and seals, such as industrial caps or seals. In some aspects, the seal, cap, or lid provides air-tight storage of the liquid or other matter contained within the container. In some aspects, the capping or closing or sealing is carried out by attaching a cap or lid to an opening of the container, such as an outlet designed for dispensing of the liquid from the bottle or other container. In some aspects, the opening is on one end of the container, while a base of the container is on another end, the two ends separated by the body of the container. In some aspects, the capping or closing is carried out in a manner such that the attachment forms an airtight seal between the cap and the bottle. In some aspects, the capping is industrial capping. In some aspects, the capping is carried out by the same machine used to sterilize or sanitize and/or fill the bottle or other container with a liquid. Thus, in some aspects, the apparatus includes a capping mechanism for attaching a cap to an outlet of the container, such as an airtight attachment. In some aspects, the cap is sterilized or sanitized, such as by the same sterilization or sanitization process used for the container, e.g., by steam, heat, irradiation, pressure, disinfecting with water, gas, or a sterilizer, autoclaving, or a combination thereof.

7. Apparatuses and Machines

Also provided are apparatuses and machines configured to carry out the methods and/or for use in the methods. In some aspects, the apparatus or machine is operated by a service provider carrying out the method or its agent, and/or by a customer or its agent. In some aspects, the apparatuses include industrial-grade bottle washing, filling, sterilizing/sanitizing, and/or capping machines, such as those configured for the decontaminating, filling, and/or capping of gallon or multi-gallon water bottles for storage and/or dispensing of drinking water. In some embodiments, the apparatuses are kiosks or vending machines, which receive, sanitize or sterilize, fill, and/or cap containers, such as bottles, and return the same to a customer.

In some embodiments, the apparatus includes a sterilization or sanitization station, configured to receive and sterilize or sanitize the container, e.g., bottle. In some aspects, the sterilization or sanitization is not carried out by treatment with ozone. In some embodiments, the apparatus further includes a filling station configured to receive the container following sterilization or sanitizing, for filling with a liquid, such as drinking water. In some embodiments, the apparatus includes a liquid source, configured to supply the liquid to the bottle when present in the filling station. In some aspects, it further includes a liquid purification station, configured to purify tap water or other liquid prior to supply to the container via the liquid source. Thus, in some aspects, the purification station is operatively connected to the liquid source. In some aspects, the apparatus further includes a capping mechanism, configured to attach a cap, seal, or lid to the container when inserted into the appropriate location in the apparatus. In some aspects, the capping is airtight.

In some embodiments, the apparatus includes one or more conveyer assemblies, elevator mechanisms, container rail guide assembly, locking collars, configured to move the container within the apparatus to the appropriate location or locations, such as in an automated fashion, e.g., in response to payment, for sterilization or sanitation, filling, and capping.

In some embodiments, the apparatus includes a vending shelf and/or vending door, configured to dispense the container to the customer following sterilization or sanitization, filling, and/or capping. In some embodiments, the vending shelf is configured behind a locking vending door, such that the bottle or other container may not be accessed prior to opening of the door, which in some aspects occurs in response to an action of the apparatus, such as payment by the customer and/or completion of one or more of the various steps carried out by the apparatus. In some examples, the guide rail assembly and locking collars retain the containers on conveyor assemblies in a controlled manner and allow movement, e.g., incremental movement, of the container or containers towards the vending door or shelf in response to completion of one or more steps. In some aspects, such features are configured such that a customer may receive the same container inserted into the machine by the customer or operator of the machine. In some aspects, the machine or apparatus includes a mechanism for reading and interpreting an identification code associated with the bottle or customer, such as a bar code, to facilitate the return of the same bottle to the customer.

In some embodiments, the apparatus includes a payment acceptor, configured to accept payment from a customer. In some aspects, the payment acceptor includes a credit card, debit card, or pre-paid card acceptor or electronic purchase facilitation device, such as one connected by Ethernet, landline, wireless connection, or cellular services for communication with a bank or other agency, to allow a customer to make purchases and receive credits from the apparatus in association with the purchase of bottles and associated services, such as filling, sterilizing/sanitizing, and capping of the bottles, and/or for return of used bottles. In some aspects, the payment acceptor includes a cash acceptor. In some aspects, the apparatus further includes a payment dispenser, such as a cash or change or credit dispenser.

In some embodiments, the apparatus includes one or more controllers and/or sensors, such as those permitting all or certain steps of the methods to be carried out in an automated fashion and/or in response to the completion of other steps or input by the user or customer. In some aspects, the controller is operatively connected to the sterilization or sanitization station, liquid source, capping device, conveyer assemblies, elevator mechanisms, container rail guide assembly, locking collars, vending shelf, vending door, and/or payment acceptor and/or dispenser. In some embodiments, such connection is facilitated by way of connection to one or more sensors. In some aspects, the connection renders the controller operative to cause one or more appropriate action of the apparatus, e.g., sterilization or sanitization, filling of the bottle, upon completion of another step or input, such as upon receipt of payment by the payment acceptor and/or input from the customer or user via a screen.

In some embodiments, the apparatus further includes a screen, such as a touch screen, and/or a keyboard or keypad or other mechanism for interaction between the customer or user and the apparatus.

In some embodiments, the apparatuses carry out one or more of the method steps in an automated fashion. In some aspects, the apparatuses include a controller, such as a computer and/or control panel, operatively connected to the various features of the apparatus, such that the various steps are controlled in an automated fashion. In some embodiments, the machines or apparatuses are designed for carrying out the steps manually, such as by actions of the user such as the service provider carrying out the methods and/or the customer.

Exemplary machines and apparatuses for sterilization or sanitization and/or other method steps include large bottle washers, fillers, and capper machines of the TritonLine™, available from Norland International, such as the Triton450™ (see World Wide Web at www.triton450.com), and/or the BWF60 Washer/Filler/Capper, available from Norland International (see World Wide Web at www.norlandintl.com/BWF60-washer-filler-capper-large-bottle-water-equipment).

Exemplary known apparatuses for receiving, dispensing, filling, removing contaminants from, and/or capping containers such as water bottles, and/or for the generation of containers, and/or purification of liquids and water, include those described in U.S. Patent Publication Nos. US 2012/00222938 A1, Rose et al., Sep. 6, 2012 and US 2013/0240084 A1, Carter and Bumgarner, Sep. 19, 2013, and U.S.

Pat. No. 8,360,272, Piersant et al., Jan. 29, 2013, Carter et al., and those available from Water Business USA (WB USA, see World Wide Web at www.waterbusiness.com/products/commercial), including water filling equipment including the Automatic Bottling Line Semi Automatic Bottling line, CSD5 Bottle Blow Molding Machine, water purification apparatuses including Diamond Skid R.O. system, Diamond Skid XL R.O. system, Export Skid R.O. System, Lite Commercial R.O. System, AS1000 Water Bagging/Sachet Machine, Easy Fill Manual Bottling System, Rinse & Fill Manual Fill Station, Bottle Fill Station, BottleRinse™ water bottle rinsing station, Window Water Vending Unit (WindowVend™), and those available from Jiangmen Crystal Water Tech Co., Ltd (see World Wide Web gdangel.en.alibaba.com), including automated and micro computer filling machines, washing machines, and/or cap pulling and/or sealing machines, and complete production lines.

The invention claimed is:

1. A method comprising:
   determining whether a recycling code number on a bottle of a consumer is a 3, 6, or 7 recycling code number;
   in response to a determination that the recycling code number is not a 3, 6, or 7 recycling code number:
      sanitizing the bottle using steam that has a temperature of 100° C. to 121° C. for a duration of 5 to 10 minutes; and
      providing the sanitized bottle to the consumer; and
   in response to a determination that the recycling code number is a 3, 6, or 7 recycling code number:
      informing the consumer of the environmental or health impact of the bottle;
      providing an offer to sell, exchange, or rent to the consumer a bottle which does not have a recycling code number of 3, 6, or 7; and
      determining whether the consumer accepts the offer;
   in response to a determination that the consumer accepted the offer:
      identifying a bottle which does not have a recycling code number of 3, 6, or 7;
      sanitizing the bottle which does not have a recycling code number of 3, 6, or 7 using steam that has a temperature of 100° C. to 121° C. for a duration of 5 to 10 minutes; and
      providing the sanitized bottle to the consumer.

2. The method of claim 1, wherein the consumer owns, exchanges, or has rented the bottle that undergoes the determination of whether a recycling code number on the bottle is a 3, 6, or 7 recycling code number.

3. The method of claim 1, wherein the sanitizing is carried out in a store or the providing does not comprise delivery to a home or business owned or rented by the consumer.

4. The method of claim 1, wherein the sanitizing is carried out by inserting the bottle into a machine configured to sanitize the bottle using the steam that has a temperature of 100° C. to 121° C.

5. The method of claim 1, further comprising:
   filling the sanitized bottle with a drinkable or consumable liquid before said providing to said consumer; or
   providing a drinkable or consumable liquid dispensing station to the consumer with which to fill the sanitized bottle with the drinkable or consumable liquid,
   wherein the drinkable or consumable liquid is selected from the group consisting of drinking water, purified water, tap water, spring water, well water, rainwater, recycled water, treated water, distilled water, juice, soda, tea, a sports drink, a drink with one or more nutritional supplements, a meal replacement, formula, milk, beer, wine, liquor, and medicine.

6. The method of claim 5, wherein the sanitizing and filling are carried out by inserting the bottle into a machine, wherein the machine is programmed to sanitize and fill the bottle.

7. The method of claim 5, further comprising capping the filled bottle prior to said providing the bottle to the consumer.

8. The method of claim 7, wherein the capping comprises attaching a bottle cap to an outlet designed for dispensing of the liquid from the bottle, wherein said attachment forms an airtight seal between the bottle cap and the bottle.

9. The method of claim 1, wherein the sanitized bottle comprises an identifier for association of the bottle with the consumer or the method further comprises applying an identifier to the bottle for association of the bottle with the consumer.

10. The method of claim 1, wherein the sanitized bottle is substantially free of BPA.

11. The method of claim 1, further comprising accepting payment from the consumer.

12. The method of claim 11, wherein the payment is not made on a subscription basis.

13. The method of claim 1, wherein the sanitized bottle has a liquid holding capacity of at least 1 gallon.

14. The method of claim 8, further comprising sanitizing the bottle cap prior to capping the filled bottle.

* * * * *